United States Patent
Alvarez Hernandez

(12) 
(10) Patent No.: US 6,555,093 B2
(45) Date of Patent: Apr. 29, 2003

(54) COMPOSITION FOR THE TREATMENT OF HALITOSIS

(75) Inventor: Maria Alvarez Hernandez, Madrid (ES)

(73) Assignee: Biocosmetics, S.L., Madrid (ES)

(*) Notice: Subject to any disclaimer, the term of this patent is extended or adjusted under 35 U.S.C. 154(b) by 0 days.

(21) Appl. No.: 09/996,541

(22) Filed: Nov. 28, 2001

(65) Prior Publication Data

US 2002/0054859 A1 May 9, 2002

Related U.S. Application Data

(62) Division of application No. 09/601,773, filed as application No. PCT/ES98/00184 on Jun. 26, 1998, now Pat. No. 6,350,435.

(30) Foreign Application Priority Data

Feb. 6, 1998 (ES) ............................................. 9800228

(51) Int. Cl.[7] .......................... A61K 9/68; A61K 7/16; A61K 7/26
(52) U.S. Cl. ............................ 424/48; 424/49; 424/58; 424/440; 424/441; 424/195.1
(58) Field of Search .......................... 424/49, 50, 51, 424/52, 53, 54, 55, 56, 57, 58, 48, 440

(56) References Cited

U.S. PATENT DOCUMENTS

| 4,525,342 A | 6/1985 | Weiss et al. ................... 424/49 |
| 4,548,809 A | 10/1985 | Fung et al. ..................... 424/52 |
| 5,900,251 A | 5/1999 | Raissen ....................... 424/456 |
| 6,350,435 B1 * | 2/2002 | Alvarez Hernandez ...... 424/48 |

FOREIGN PATENT DOCUMENTS

| DE | 2611895 | 9/1977 |
| DE | 3844632 | 6/1990 |
| GB | 601801 | 5/1948 |
| JP | 09059138 | 3/1997 |
| WO | 9512380 | 5/1995 |

OTHER PUBLICATIONS

Patent Abstract of Japan Publication No. 09059138 Dated Mar. 4, 1997.

Yaegaki, K. et al. "Effects of a Two–Phase Oil–Water Mouth Wash on Halitosis" Clinical Preventive Dentistry, vol. 14, No. 1, pp. 5–9, (1992).

* cited by examiner

*Primary Examiner*—Zohreh Fay
*Assistant Examiner*—Brian-Yong S. Kwon
(74) *Attorney, Agent, or Firm*—Ladas & Parry

(57) ABSTRACT

The composition comprises a mixture of olive oil (*Olea europea* L.) and parsley oil (*Petroselinum sativum* Hoffm., *Petroselinum crispum* Mill., *Carum petroselinum* Benth & Hooker), in a ratio of olive oil: parsley oil, by weight, comprised between 1 and 7. Additionally the composition may contain other vegetable oils, mint oil, menthol and chlorophyll. These compositions may be presented in several forms including sweets, chewing-gum, dentifrice paste, mouthwashes and pharmaceutical compositions, especially as soft gelatine capsules, for which purpose they incorporate the suitable additives, vehicles and excipients for its processing in the desired form of presentation. The composition is suitable for the treatment of halitosis.

24 Claims, No Drawings

COMPOSITION FOR THE TREATMENT OF HALITOSIS

This application is a Division of Ser. No. 09/601,773 Aug. 7, 2000, patented, U.S. Pat. No. 6,350,435, which is a 371 of PCT/ES98/00184 Jun. 26, 1998.

FIELD OF THE INVENTION

This invention refers to a composition suitable for the treatment of halitosis which comprises a mixture of olive and parsley oils, and to presentations thereof.

BACKGROUND TO THE INVENTION

Halitosis, or bad breath, are terms employed to describe unpleasant odours detectable in exhaled air. This is a problem which affects many people, those who suffer it and those surrounding the former which, often, perceive the situation as socially unacceptable.

Halitosis is produced by the production and liberation of volatile compounds, mainly volatile derivatives of sulphur, such as hydrogen sulphide and methyl-mercaptane and, according to the localisation of the origin of the unpleasant odour, it can be classified as oral (localised in lips, tongue, teeth, dental prosthetic elements, periodontal tissues, oropharynx) or non-oral [caused by diseases of the respiratory tract, systemic diseases (hepatic dysfunction, cirrhosis, diabetic ketoacidosis, carcinomas and certain metabolic diseases in which an enzymatic anomaly occurs), diseases of the gastrointestinal tract and certain foods, drinks, tobacco and medicaments).

There are several treatments to combat halitosis, some are based on the administration of synthetic products, while others are based on the administration of natural products. Of the latter, the use of parsley leaves together with parsley oil or sunflower oil is a well know method to combat halitosis.

Notwithstanding, due to the widespread extent of halitosis among the population, further research has been conducted in order to obtain new compositions which enrich the set of remedies available to combat said disorder. It has now been discovered that, surprisingly, the combination of olive oil and parsley oil effectively combats halitosis. Additionally, it has been discovered that the addition to said mixture of olive and parsley oil of other vegetable oils, and in particular, mint oil, chlorophyll and menthol, not only effectively combats halitosis, but also provides a very pleasant taste and sensation of freshness. This composition is suitable for the elaboration of several forms of presentation of the same, including pharmaceutical compositions destined to the treatment of halitosis.

DETAILED DESCRIPTION OF THE INVENTION

This invention provides a suitable composition for the treatment of halitosis, from now on referred to as the composition of the invention, which comprises a mixture of olive and parsley oils, in a ratio of olive oil parsley oil, by weight, comprised between 1 and 7.

The olive is the fruit of the olive tree (*Olea europea* L.) which belongs to the Oleaceae family. Apart from water, oil, carbohydrates and proteins, the olive contains numerous minerals, particularly calcium, several organic acids and vitamins A, $B_1$, $B_2$ and pp. Olive oil, extracted from the pulp of the olive, is constituted essentially by glycerides of oleic acid (70%) and of other acids in a lesser proportion, such as those of linoleic, palmitic, linolenic and arachidonic acid, and is usually employed in cookery.

Parsley (*Petroselinum sativum* Hoffm., *Petroselinum crispum* Mill., or *Carum petroselinum* Benth & Hooker) belongs to the Umbelliferae family. Its seeds, leaves and roots are used. Its fragrance and taste seem to be due to an essence of complex and variable composition, which contains apiol, apioside and mirysticin. The main ingredients comprise volatile oils, fatty oils, flavonoids, vitamins A and C and minerals, especially iron, calcium, phosphorous and manganese. It is known for its diuretic, carminative, digestive, antispasmodic and nutritive effects, as well as for its stimulating effect upon the uterine muscle. It is widely used in cooking as well as in the treatment of urinary infections and stones, oedema, gastric disorders and anaemia. Parsley essential oil is employed in the elaboration of the composition object of the present invention.

Nothing in the state of the art suggests that the combination of olive and parsley oils, in the proportions envisaged in this description, could be effective in the treatment of halitosis.

The composition of the invention may also contain another or other vegetable oils, including, but without being limited to, the following: avocado oil, basil oil, custard apple tree oil, borage oil, camomile oil, hemp oil, safflower oil, cajeput tree oil, cedar oil, cypress oil, coconut oil, rapeseed oil, geranium oil, sunflower oil, pink evening primrose oil, jojoba oil, lanolin oil, lavender oil, lemon oil, linseed oil, peppermint oil, evening primrose oil, palm oil, rosewood oil, pineapple oil, primrose oil, castor oil, rosemary oil, sage oil, sandalwood oil, soy oil, tea tree oil, wheat germ oil, grapeseed oil and vetiver oil. These vegetable oils can be added to the mixture of olive and parsley oils in variable quantities.

Additionally, the composition of the invention may contain other products which contribute to improve its taste or flavour, or to render beneficial effects. Particularly, it has been observed that the addition of mint oil, menthol and chlorophyll to the mixture of olive and parsley oils described above, not only effectively combats halitosis, but also provides a very pleasant taste and freshness. These products can be added to the mixture in variable amounts.

In a specific embodiment of the invention, a suitable composition is provided for the treatment of halitosis, which comprises:

| Component | % by weight in relation to the total |
|---|---|
| Olive oil | 54–89 |
| Parsley oil | 5–20 |
| Mint oil | 5–20 |
| Chlorophyll | 1–5 |
| Menthol | 0–1 |

The term "mint" as used in this description includes several species of plants belonging to the genus *Mentha*, of the Labiatae family. The genus *Mentha* is one of the most complex in the plant kingdom due to the numerous natural hybrids which originate from the spontaneous crossing of the species, which, in general, can be classified into spiked mints (having flowers in a non-foliated terminal spike) and low mints (the flowers are arranged in clusters forming separate whorls in petiolated leaves). The genus Mentha includes species such as *M. rotundifolia* L., *M. viridis* L., *M. crispata* Schard, *M. longifolia* L., *M. pulegium* L., *M. arvensis* L., *M. piperita* L. and *M. aquatica* L. Usually the leaves are used. Their main ingredients are volatile oils and tannins. Their carminative and stimulatory action upon digestion is an added value to the composition provided by this invention.

Menthol is a monocyclic, optically active terpenoid oil present in the essence of mint.

Chlorophyll is the green pigment of plants.

The composition object of this invention is effective against halitosis and provides a clean and natural breath for many hours, yielding not only a pleasant taste and freshness to the mouth, but also neutralising unpleasant taste at its source. Although it is not the intention to be attached to any theory, it is believed that the volatile sulphur containing compounds responsible for the unpleasant odour are soluble in vegetable oils present in the composition of the invention, which in turn coat the chylomicron particles avoiding the absorption of the precursors of the volatile sulphur containing compounds at the small intestine, hence avoiding their excretion via the lungs. Parsley oil seems to stimulate the digestive apparatus, it enhances the effect of the vegetable oils making even more difficult the intestinal absorption of volatile sulphur containing compounds, and it improves the symptoms of gastrointestinal diseases which cause halitosis.

The addition of mint, chlorophyll and menthol enhances the neutralizing action of the mixture of parsley oil and olive oil, it increases the effect of the vegetable oils which solubilise the volatile compounds and, additionally, has a positive effect upon the user, who feels a lasting sensation of freshness which extends throughout the whole protection period of the product, which is of approximately 8 hours.

The composition of the invention can be prepared by mixing and homogenising the different components in the appropriate amounts.

The composition of the invention can be presented in several forms, including, capsules, soft gelatine capsules, sweets, chewing-gum, dentifrice, mouthwash and pharmaceutical compositions, for the purpose of which the suitable additives, vehicles and excipients for the processing in the desired form of presentation, can be incorporated. Additionally, if it is so desired, these compositions may contain anticaries, antibacterial and antiseptic agents.

In a specific embodiment, the invention provides a pharmaceutical composition which comprises said composition of the invention together with pharmaceutically acceptable excipients which include the substances usually employed in the preparation of the different galenic forms of active principles. The pharmaceutical compositions provided by this invention include, preferentially, suitable preparations for the oral administration of said composition against halitosis, including liquid oral forms, for example, elixirs, syrups, potions, etc., and solid oral forms, for example, coated tablets, capsules, pills, tablets, etc. These forms of administration of the composition against halitosis can be prepared easily by means of conventional techniques [Tratado de Farmacia Galénica, C. Fauli i Trillo, Luzán S S. A. de Ediciones, 1$^{st}$ Edition, (1993), especially Chapters 34–43]. In a preferred embodiment of this invention the form of administration of said pharmaceutical composition is in the form of gelatine capsules, preferably soft gelatine capsules (Example 2).

In another specific and preferred embodiment of this invention, the form of presentation of the composition against halitosis provided by this invention is a chewing-gum (example 3).

In another specific and preferred embodiment of this invention, the form of presentation of the composition against halitosis provided by this invention is a dentifrice paste (Example 4).

In another specific and preferred embodiment of this invention, the form of presentation of the composition against halitosis provided by this invention is a double phased oil-water mouthwash (Example 5).

The following example serve the purpose of illustrating specific embodiments of the object of the present invention, but they must not be considered to limit the scope of the same.

EXAMPLE 1

Preparation of a Composition Against Halitosis

A suitable composition against halitosis is prepared containing:

| Component | % by weight in relation to total |
|---|---|
| Olive oil | 66.25 |
| Parsley oil | 15.00 |
| Mint oil | 15.00 |
| Chlorophyll | 3.00 |
| Menthol | 0.75 |

The corresponding amounts of each of the components were mixed to prepare said composition. All the products used are commercial products.

EXAMPLE 2

Preparation of Soft Gelatine Capsules Suitable for the Treatment of Halitosis

Soft gelatine capsules were prepared containing 100 mg per capsule of the composition obtained in Example 1, by enceosulation of said composition in soft gelatine capsules, obtained by mixing gelatine (46 mg/capsule) and glycerine (26 mg/capsule), by conventional techniques [Tratado de Farmacia Galénica, C. Fauli i Trillo, Luzán S S. A. de Ediciones, 1$^{st}$ Edition, (1993), Chapter XLI, pages 587–592].

EXAMPLE 3

Preparation of Chewing-gum to Combat Halitosis

Chewing gum is prepared in the form of coated tablets suitable to combat halitosis, having the following composition:

| Component | % by weight in relation to total |
|---|---|
| Olive oil | 5 |
| Parsley oil | 1 |
| Mint oil | 1 |
| Chlorophyll | 0.2 |
| Xylitol | 10.00 |
| Sorbitol | 55.15 |
| Base gum | 18.25 |
| Maltitol syrup | 8.59 |
| Lecithin | 0.55 |
| Dicalcium phosphate | 0.13 |
| Carnauba wax | 0.04 |
| Confectionery sugar | 0.09 |

All the products used are commercial products. In the preparation of the chewing-gums, the process described hereunder was followed. The base gum is added to a jacketed mixer, fitted with a blade stirrer, preheated to approximately 65° C. When the base begins to soften sorbitol starts being added (in powdered form), adding approximately 50–60% of the total sorbitol, and it is mixed. Subsequently approximately one third of the maltitol syrup is added and blended in. After this approximately 10% of the sorbitol (powder)is added, mixed, and a second third of the maltitol syrup is added, mixed, and 10% of the sorbitol (powder), xylitol, lecithin are added and all is mixed. After this, the remaining third of the maltitol syrup is added, mixed, and the rest of the sorbitol (powder) is added, mixed, and the mint essential oil is added and mixed.

After finishing, the batch of chewing gum produced is loaded down into suitable containers and transported to a chewing-gum laminator.

The batch produced is loaded into a double-spindle pre-extruder which feeds the extruder of the laminator. The chewing-gum is extruded as a wide, thick sheet, which is powdered on both sides with calcium carbonate to prevent stickiness during lamination. Each set of rollers of the laminator reduces the thickness of the chewing-gum until the desired size for the tablet is achieved. The sheet of chewing gum is then introduced into two sets of rollers for its cutting, the first cutting it in strips, and the second cutting across to produce the tablets.

The tablets are collected in trays, are weighed and are allowed to cure in a cold room for approximately 24 hours.

For the coating of the tablets, a specific amount of pre-weighed tablets is placed in each coating well. The coating of the tablets is begun with a 70% solution of sorbitol and sorbitol (fine powder). Subsequently the amount of parsley essential oil and olive oil is weighed, absorbed on dicalcium phosphate, suitable for each coating well, and it is dispensed with sorbitol powder. The mixture is added in increasing amounts over the wet chewing-gum tablets. Subsequently the taste-enhancer is added over the coating layer together with the chlorophyll dispersed in a solution of sorbitol.

When the tablets have reached the desired weight they are polished with powdered carnauba wax, are placed in trays and are dried. The dry tablets are polished again with a mixture of carnauba wax and bee's wax, and are glazed to protect them from moisture.

EXAMPLE 4

Preparation of a Dentifrice Paste Suitable to Combat Halitosis

A dentifrice paste suitable to combat halitosis is prepared, which has the following composition:

| Component | % by weight in relation to total |
|---|---|
| Olive oil | 5 |
| Parsley oil | 1 |
| Chlorophyll | 0.2 |
| Sorbitol | 31.48 |
| Silica | 17.8 |
| Xylitol | 10 |
| Glycerine | 5 |
| Tetrapotassium pyrophosphate | 2.3 |
| Potassium phosphate | 0.9 |
| Xanthan gum | 0.575 |
| Sodium fluoride | 0.22 |

-continued

| Component | % by weight in relation to total |
|---|---|
| Saccharin | 0.13 |
| Diazolidinyl urea | 0.1 |
| Titanium dioxide | 0.09 |
| Green colorant | 0.001 |
| Water | q.s. to 100% |

The corresponding amounts of each of the components were mixed to prepare this dentifrice paste. All the products used are commercial products.

EXAMPLE 5

Preparation of a Mouthwash to Perform Mouth-washes Suitable to Combat Halitosis

A double phase oil-water mouthwash is prepared, for carrying out mouth-washes suitable for combating halitosis, which presents the following composition:

| Component | % by weight in relation to total |
|---|---|
| Olive oil | 5 |
| Parsley oil | 1 |
| Xylitol | 1 |
| Sodium fluoride | 0.05 |
| Allantoin | 0.2 |
| Sodium methylparaben | 0.12 |
| Sodium propylparaben | 0.06 |
| Hydrogenated castor oil And polyethylene glycol (PEG-40) | 0.25 |
| Chlorhexidine | 0.12 |
| Fragrance | 0.1 |
| Sodium saccharide | 0.2 |
| C.I. 42090 (E-133) | 0.001 |
| Water | 92.079 |

The corresponding amounts of each of the components were mixed to prepare this mouthwash. All the products used are commercial products.

This mouthwash is a double phased oil-water preparation because in the mouth there are hydrophobic bacteria which are only removed in a liquid lipophylic medium. This mouthwash contains fat-soluble mint essences, xylitol as anticaries agent, natural sweetener and freshener, as well as chlorhexidine (antibacterial).

What is claimed is:

1. A composition for the treatment of halitosis which comprises a mixture of olive oil (*Olea europea L.*) and parsley oil (*Petroselinum sativum* Hoffm., *Petroselinum crispum* Mill., *Carum petroselinum* Benth & Hooker), in a ratio of olive oil: parsley oil, by weight, between 1 and 7 in the form of a dentifrice paste.

2. The composition according to claim 1, further comprising a vegetable oil.

3. The composition according to claim 2, in which said vegetable oil is selected from the group consisting of avocado oil, basil oil, custard apple tree oil, borage oil, camomile oil, hemp oil, safflower oil, cajeput tree oil, cedar oil, cypress oil, coconut oil, rapeseed oil, geranium oil, sunflower oil, pink evening primrose oil, jojoba oil, lanolin oil, lavender oil, lemon oil, linseed oil, peppermint oil, evening primrose oil, palm oil, rosewood oil, pineapple oil, primrose oil, castor oil, rosemary oil, sage oil, sandalwood oil, soy oil, tea tree oil, wheat germ oil, grape-seed oil, vetiver oil and mixtures thereof.

4. The composition according to claim 1, further comprising mint oil, menthol and chlorophyll.

5. The composition according to claim 4, which comprises:

| Component | % by weight in relation to the total |
|---|---|
| Olive oil | 54–89 |
| Parsley oil | 5–20 |
| Mint oil | 5–20 |
| Chlorophyll | 1–5 and |
| Menthol | 0–1. |

6. The composition according to claim 5, which comprises:

| Component | % by weight in relation to total |
|---|---|
| Olive oil | 66.25 |
| Parsley oil | 15.00 |
| Mint oil | 15.00 |
| Chlorophyll | 3.00 and |
| Menthol | 0.75. |

7. The pharmaceutical composition which comprises a composition according to claim 1 and a pharmaceutically acceptable excipient.

8. The composition according to claim 1, which additionally comprises an agent selected from the group consisting of an antibacterial agent, an anticaries agent and an antiseptic.

9. The composition according to claim 1, further comprising tea tree oil and mint oil.

10. The pharmaceutical composition which comprises a composition according to claim 2 and a pharmaceutically acceptable excipient.

11. The pharmaceutical composition which comprises a composition according to claim 3 and a pharmaceutically acceptable excipient.

12. A pharmaceutical composition which comprises a composition according to claim 4 and a pharmaceutically acceptable excipient.

13. A composition for the treatment of halitosis which comprises a mixture of olive oil (*Olea europea L.*) and parsley oil (*Petroselinum sativum* Hoffm., *Petroselinum crispum* Mill., *Carum petroselinum* Benth & Hooker), in a ratio of olive oil: parsley oil, by weight, between 1 and 7 in the form of a mouthwash.

14. The composition according to claim 13, further comprising a vegetable oil.

15. The composition according to claim 14, in which said vegetable oil is selected from the group consisting of avocado oil, basil oil, custard apple tree oil, borage oil, camomile oil, hemp oil, safflower oil, cajeput tree oil, cedar oil, cypress oil, coconut oil, rapeseed oil, geranium oil, sunflower oil, pink evening primrose oil, jojoba oil, lanolin oil, lavender oil, lemon oil, linseed oil, peppermint oil, evening primrose oil, palm oil, rosewood oil, pineapple oil, primrose oil, castor oil, rosemary oil, sage oil, sandalwood oil, soy oil, tea tree oil, wheat germ oil, grape-seed oil, vetiver oil and mixtures thereof.

16. The composition according to claim 13, further comprising mint oil, menthol and chlorophyll.

17. The composition according to claim 16, which comprises:

| Component | % by weight in relation to the total |
|---|---|
| Olive oil | 54–89 |
| Parsley oil | 5–20 |
| Mint oil | 5–20 |
| Chlorophyll | 1–5 and |
| Menthol | 0–1. |

18. The composition according to claim 17, which comprises:

| Component | % by weight in relation to total |
|---|---|
| Olive oil | 66.25 |
| Parsley oil | 15.00 |
| Mint oil | 15.00 |
| Chlorophyll | 3.00 and |
| Menthol | 0.75. |

19. A pharmaceutical composition which comprises a composition according to claim 13 together with a pharmaceutically acceptable excipient.

20. The composition according to claim 19 further comprising an agent selected from the group consisting of an antibacterial agent, an anticaries agent and an antiseptic.

21. The composition according to claim 13, further comprising tea tree oil and mint oil.

22. A pharmaceutical composition which comprises a composition according to claim 14 together with a pharmaceutically acceptable excipient.

23. A pharmaceutical composition which comprises a composition according to claim 15 together with a pharmaceutically acceptable excipient.

24. A pharmaceutical composition which comprises a composition according to claim 16 together with a pharmaceutically acceptable excipient.

* * * * *